United States Patent
Sloan

(10) Patent No.: US 11,330,793 B1
(45) Date of Patent: May 17, 2022

(54) WIRELESS ACTIVITY AND ENVIRONMENTAL MONITORING DEVICE AND SYSTEM FOR SMALL, CAGED MAMMALS

(71) Applicant: Andrew Michael Sloan, Westminster, CO (US)

(72) Inventor: Andrew Michael Sloan, Westminster, CO (US)

(*) Notice: Subject to any disclaimer, the term of this patent is extended or adjusted under 35 U.S.C. 154(b) by 481 days.

(21) Appl. No.: 16/398,546

(22) Filed: Apr. 30, 2019

Related U.S. Application Data

(60) Provisional application No. 62/665,064, filed on May 1, 2018.

(51) Int. Cl.

| | | |
|---|---|---|
| *A01K 1/03* | (2006.01) | |
| *G06F 3/02* | (2006.01) | |
| *H04N 5/33* | (2006.01) | |
| *A61B 5/00* | (2006.01) | |
| *A61B 5/01* | (2006.01) | |
| *A01K 29/00* | (2006.01) | |
| *H02J 7/00* | (2006.01) | |
| *H02J 7/02* | (2016.01) | |
| *H04Q 9/00* | (2006.01) | |
| *H04W 84/18* | (2009.01) | |

(52) U.S. Cl.
CPC ............ *A01K 1/031* (2013.01); *A01K 29/005* (2013.01); *A61B 5/0008* (2013.01); *A61B 5/0013* (2013.01); *A61B 5/0077* (2013.01); *A61B 5/015* (2013.01); *G06F 3/02* (2013.01); *H02J 7/00* (2013.01); *H02J 7/0047* (2013.01); *H02J 7/025* (2013.01); *H04N 5/33* (2013.01); *H04Q 9/00* (2013.01); *A61B 2503/40* (2013.01); *A61B 2560/0214* (2013.01); *A61B 2560/0252* (2013.01); *A61B 2562/029* (2013.01); *H04Q 2209/40* (2013.01); *H04W 84/18* (2013.01)

(58) Field of Classification Search
CPC .............................. A01K 1/031; A61B 5/0059
See application file for complete search history.

(56) References Cited

U.S. PATENT DOCUMENTS

| | | | | |
|---|---|---|---|---|
| 2004/0217858 | A1* | 11/2004 | Ingley, III | G08B 25/10 340/539.26 |
| 2013/0226018 | A1* | 8/2013 | Kumar | A61B 5/335 600/515 |
| 2015/0022352 | A1* | 1/2015 | Gettings | G01D 7/00 340/540 |
| 2016/0213317 | A1* | 7/2016 | Richardson | A61B 5/1135 |
| 2020/0092681 | A1* | 3/2020 | Shapiro | G16H 10/60 |

* cited by examiner

*Primary Examiner* — Fabricio R Murillo Garcia
(74) *Attorney, Agent, or Firm* — Plager Schack LLP; Mark H. Plager; Stephen Hallberg

(57) ABSTRACT

A wireless activity and environmental monitoring system and device for small, caged mammals is disclosed which combines all sensing, processing, and communication functions of a small animal home cage health and monitoring system into a device small enough in volume that it can be unobtrusively placed in animals' home cages. The device is battery-powered and communicates wirelessly and requires no extraneous supporting hardware for operation.

10 Claims, 5 Drawing Sheets

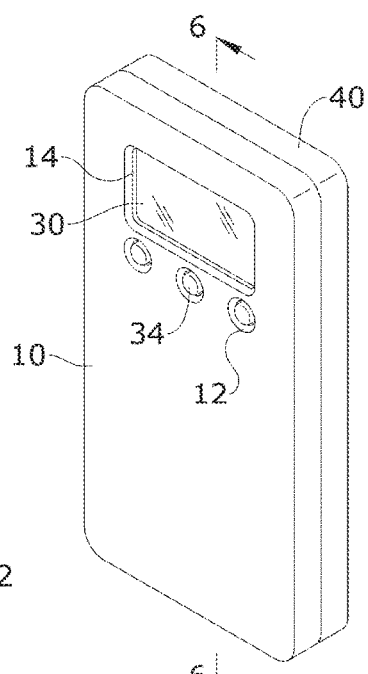
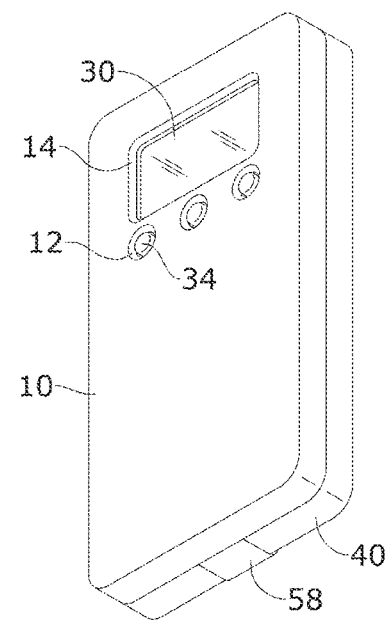
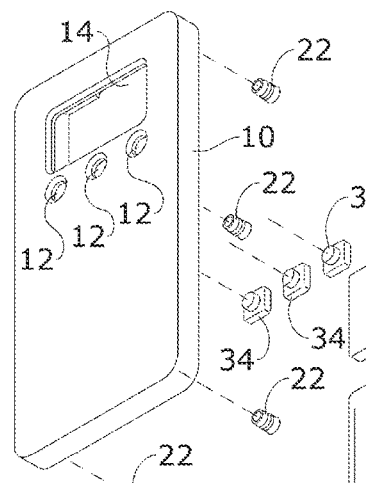
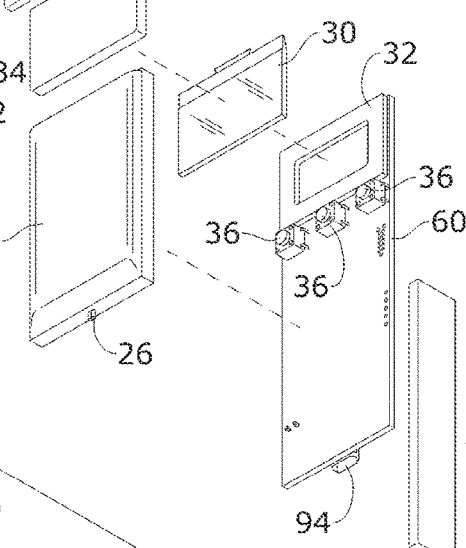
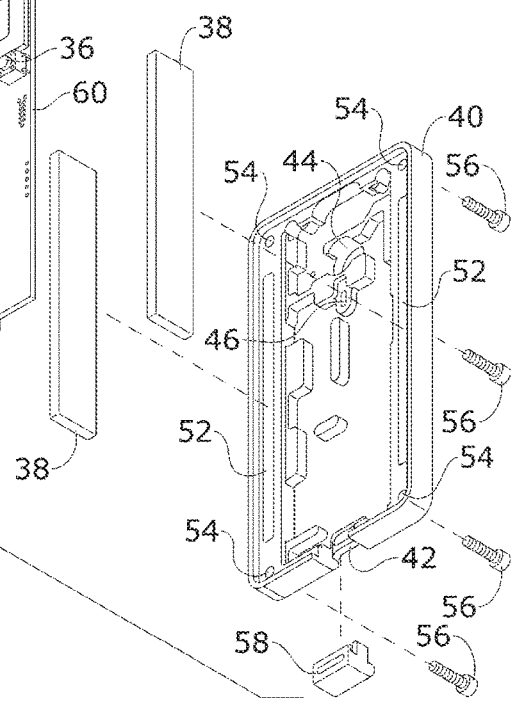
FIG.1
FIG.2
FIG.3

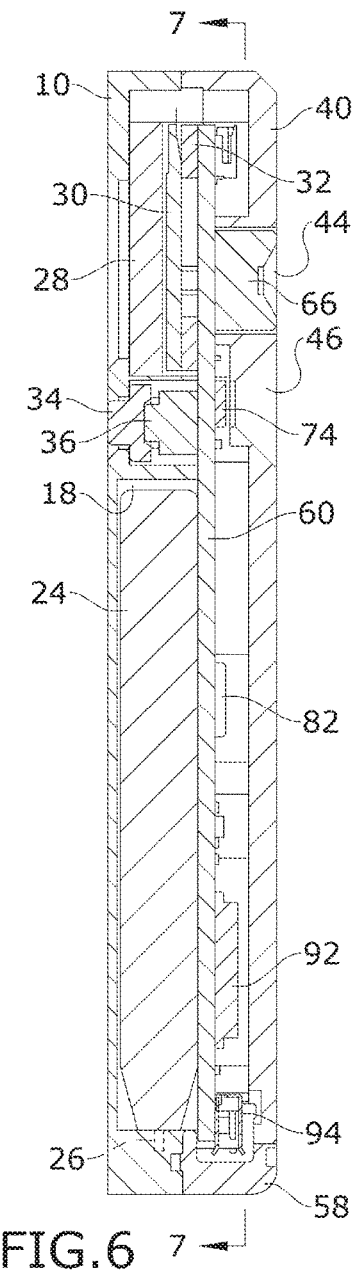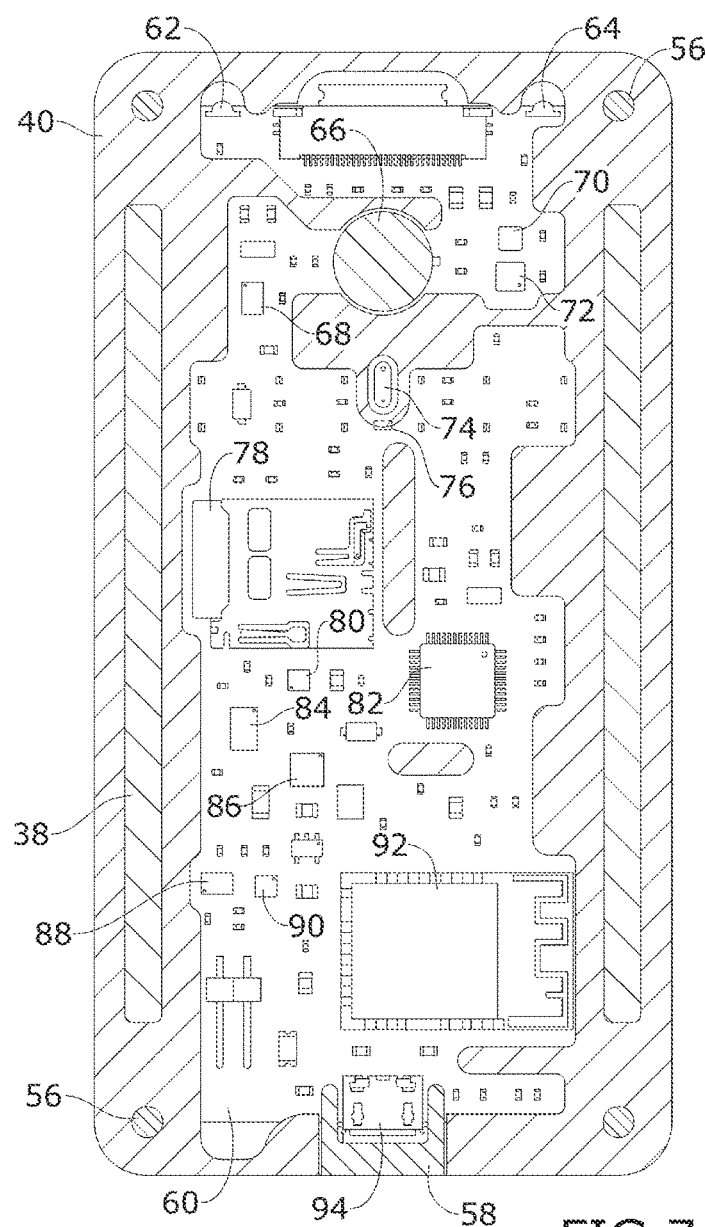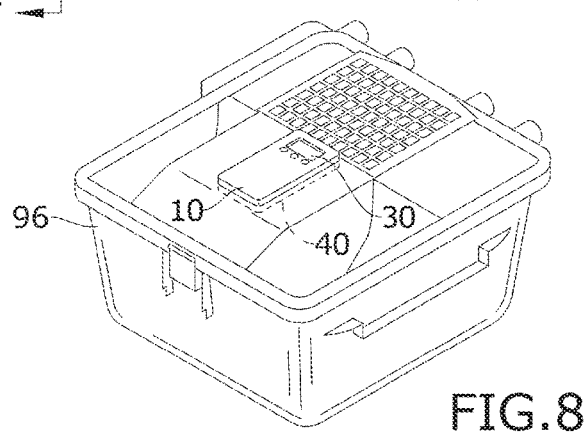
FIG.6
FIG.7
FIG.8

US 11,330,793 B1

WIRELESS ACTIVITY AND ENVIRONMENTAL MONITORING DEVICE AND SYSTEM FOR SMALL, CAGED MAMMALS

CLAIM OF BENEFIT TO PRIOR APPLICATION

This application claims benefit to U.S. Provisional Patent Application 62/665,064, entitled "A WIRELESS ACTIVITY AND ENVIRONMENTAL MONITORING DEVICE AND SYSTEM FOR SMALL, CAGED MAMMALS," filed May 1, 2018. The U.S. Provisional Patent Application 62/665,064 is incorporated herein by reference.

BACKGROUND

Embodiments of the invention described in this specification relate generally to monitoring systems, and more particularly, to wireless activity and environmental monitoring systems and devices for small, caged mammals.

A major factor slowing the pace of in vivo biomedical research is the difficulty in standardizing and reproducing health and behavior assessments. In a survey done by Nature in 2016, ~70% of biology and medicine researchers reported being unable to reproduce others' results, and an astonishing ~60% reported being unable to even reproduce their own. This "reproducibility crisis" is a problem in biomedical research. A growing body of literature suggests that at least some part of the "reproducibility crisis" may stem from an outsized influence of nuisance factors. Uncontrolled factors such as ambient temperature, humidity, lighting, and test timing also contribute to result variability, but the most significant factor influencing behavioral assessment variability is the identity of the experimenter, often contributing more variability than animal genotype. Even when laboratories go to heroic lengths to standardize testing between laboratories, significant experimenter effects still exist. These results have led to the relatively recent proliferation of automated home-cage testing solutions, which seek to remove or reduce experimenter handling effects and produce more etiologically accurate data.

All current small animal home cage health and environmental monitoring solutions share several key limitations. First, most systems cannot be mounted in vivariums' existing ventilated cage systems and require additional vivarium space. Having the cages removed from ventilation also increases risk from moisture, heat, ammonia, and carbon dioxide build-up, as well as biosecurity risk. Second, most systems require wired connections for power and computer control and, particularly for high definition video tracking systems, real-time analysis and tracking is bandwidth-limited to a single system per computer. Third, the high complexity and large size of the systems increase device costs such that they are generally capital expenditures. These limitations have combined to prevent most researchers from easily adopting home cage assessment techniques.

Existing small animal home cage monitoring systems are overly large, do not generalize to existing vivarium cage systems, require high-bandwidth wired communication, and require a standard computer for operation.

Therefore, what is needed is a way to provide all the functions of conventional small animal home cage health and monitoring systems in a device that is battery-powered, communicates wirelessly, requires no extraneous supporting hardware for operation, and is small enough in volume that it can be unobtrusively placed in animals' home cages.

BRIEF DESCRIPTION

A novel wireless activity and environmental monitoring device and system for small, caged mammals is disclosed which combines all sensing, processing, and communication functions of a small animal home cage health and monitoring system into a device that is battery-powered, communicates wirelessly, requires no extraneous supporting hardware for operation, and is small enough in volume to be unobtrusively placed in animals' home cages.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein:

FIG. 1 conceptually illustrates a top perspective view of a wireless activity and environmental monitoring device in some embodiments.

FIG. 2 conceptually illustrates a bottom perspective view of a wireless activity and environmental monitoring device in some embodiments.

FIG. 3 conceptually illustrates a front perspective exploded view of a wireless activity and environmental monitoring device in some embodiments.

FIG. 6 is a section view of the wireless activity and environmental monitoring device taken along line 6-6 in FIG. 1.

FIG. 7 is a section view of the wireless activity and environmental monitoring device taken along line 7-7 in FIG. 6.

FIG. 8 conceptually illustrates a perspective view of a small mammal cage on which to utilize a wireless activity and environmental monitoring device in some embodiments.

DETAILED DESCRIPTION

Figure 4:
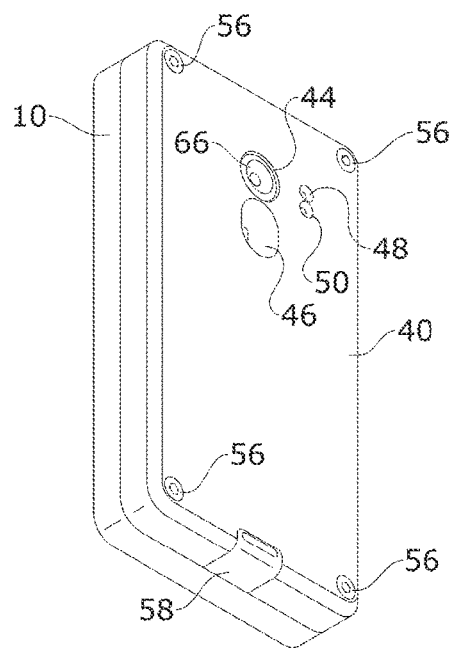
FIG. 4 conceptually illustrates a rear perspective view of a wireless activity and environmental monitoring device in some embodiments.

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments of the invention include a novel wireless activity and environmental monitoring device and system for small, caged mammals is disclosed which combines all sensing, processing, and communication functions of a small animal home cage health and monitoring system into a device that is battery-powered, communicates wirelessly, requires no extraneous supporting hardware for operation, and is small enough in volume to be unobtrusively placed in animals' home cages.

As stated above, the problematic "reproducibility crisis" in biomedical research may stem in part from nuisance and other ambient factors which influence behavioral assessment variability in research for small, caged mammals in their home cage. Yet the most significant factor influencing behavioral assessment variability is the identity of the experimenter, often contributing more variability than animal genotype. One way of addressing this issue is to remove experimenter handling as much as possible. However, the existing conventional small animal home cage health and environmental monitoring solutions share several key limitations that have combined to prevent most researchers from easily adopting home cage assessment techniques. Embodiments of the wireless activity and environmental monitoring device and system described in this specification solve such problems by providing a device that is designed with a small enough form factor to be mounted inside an animal's home cage in order to discretely and unobtrusively perform automated monitoring of small animal health and activity. In some embodiments, the wireless activity and environmental monitoring device and system records information about animal activity and vital statistics using integrated thermographic, barometric, temperature, humidity, and photosensitive sensors, and processes and transmits recorded data using integrated micro-controller and communication components.

Embodiments of the wireless activity and environmental monitoring device and system for small, caged mammals described in this specification differ from and improve upon currently existing options. In particular, some embodiments of the wireless activity and environmental monitoring device differ from conventional home cage assessment techniques and systems by employing a unique combination of thermographic and environment sensors, battery operation, and wireless communication to unobtrusively monitor animals in their home cages. Unlike the existing home cage monitoring systems, which generally position cameras and sensors outside of animals' home cages and require elaborate supporting hardware for operation, such as controlled lighting systems or field-emitting coils, as well as using wired connections for communication and power that interfere with vivarium cage hygiene procedures, the wireless activity and environmental monitoring device for small, caged mammals is designed to be mounted on the inside surface of an animal's home cage. This is possible because the wireless activity and environmental monitoring device for small, caged mammals of the present disclosure combines all sensing, processing, and communication functions of a small animal home cage health and monitoring system into a proportionally small device that can be unobtrusively placed in animals' home cages. Furthermore, the device is battery-powered and communicates wirelessly, thereby eliminating wired power and communications.

The wireless activity and environmental monitoring device and system for small, caged mammals of the present disclosure may be comprised of the following elements. This list of possible constituent elements is intended to be exemplary only and it is not intended that this list be used to limit the wireless activity and environmental monitoring device and system for small, caged mammals of the present application to just these elements. Persons having ordinary skill in the art relevant to the present disclosure may understand there to be equivalent elements that may be substituted within the present disclosure without changing the essential function or operation of the wireless activity and environmental monitoring device and system for small, caged mammals.

1. Wireless communication-enabled micro-controller
2. USB serial interface
3. Data memory storage
4. User input interface
5. Display screen (such as an OLED display)
6. Ambient light photo-transistor
7. Thermographic sensor
8. Distance ranging sensor
9. Temperature/barometric pressure/humidity sensor ("T/B/H sensor", and alternately referred to as a "temperature/pressure/humidity sensor" or a "T/P/H sensor")
10. Gas sensor
11. Accelerometer/magnetometer
12. Battery fuel gauge
13. Battery charge controller
14. Battery
15. Protective housing
16. Infrared transparent lens
17. Magnetic mounting
18. Interface bus (such as a serial peripheral interface (SPI) bus or an Inter-Integrated Circuit ($I^2C$))
19. Inductive charging coils The various elements of the wireless activity and environmental monitoring device and system of the present disclosure may be related in the following exemplary fashion. It is not intended to limit the scope or nature of the relationships between the various elements and the following examples are presented as illustrative examples only. A wireless communication-enabled micro-controller (1) collects data from a thermographic sensor (7), a distance ranging sensor (8), a T/B/H sensor (9), a gas sensor (10), and an accelerometer/magnetometer (11) through an interface bus (18). Data is processed and analyzed by the wireless communication-enabled micro-controller (1), saved into data memory storage (3), displayed for the user on the display screen (5), transmitted wirelessly to a network by the wireless communication-enabled micro-controller (1), and/or downloaded through the USB serial interface (2). The wireless communication-enabled micro-controller (1) monitors the user input interface (4) for user program selections. The system is powered by a battery (14), which in some embodiments is charged from the USB serial interface (2) by a battery charge controller (13). In some embodiments, the battery (14) is charged from an inductive charging coil (19) inductively coupled to an external, powered coil. Battery voltage is measured by a battery fuel gauge (12), which communicates with the wireless communication-enabled micro-controller (1) through the interface bus (18). Electrical components are combined within a protective housing (15) which includes an infrared transparent lens (16) and magnetic mounting (17) for attractive attachment to the cage.

The wireless activity and environmental monitoring device and system of the present disclosure generally works at a core level by the wireless communication-enabled micro-controller (1), which is capable of direct connection to local wireless networks for uploading data and status information. In some embodiments, the local data memory storage (3) on the device is of a nonvolatile type such as flash memory, ferroelectric random access memory (FRAM), static random access memory (SRAM), or magnetoresistive random-access memory (MRAM). In some embodiments, the wireless communication-enabled micro-controller (1) communicates with local data memory storage (3) through the interface bus (18).

In some embodiments, the thermographic sensor (7) includes either a forward-looking infrared (FLIR) camera or an array of thermopiles. In some embodiments, the thermographic sensor (7) captures multipixel radiant heat images from infrared emission within a set field of view. In some embodiments, the thermal image data (for the radiant heat images) is passed to the wireless communication-enabled micro-controller (1) through the interface bus (18). In some embodiments, animals' body surface temperatures are measured by identifying pixels with measured radiant temperature values significantly above background radiant temperature. Then, after distinguishing background radiant temperature from body surface temperatures, the animals' approximate positions within the cage are measured. In some embodiments, an animal's approximate position within the cage is measured by calculating the relative location of supra-threshold pixels within the thermographic sensor's (7) field of view.

In some embodiments, the integrated T/P/H sensor (9) measures ambient temperature, atmospheric pressure, and humidity, respectively, within the cage. In some embodiments, the ambient temperature, pressure, and humidity measurement data is passed to the wireless communication-enabled micro-controller (1) through the interface bus (18), which is either a SPI bus or an I2C circuit.

In some embodiments, the distance ranging sensor (8) measures the distance from the wireless activity and environmental monitoring device to the nearest perpendicular opposing surface. In some embodiments, the distance ranging sensor technology can be sonic- or light-based. In some embodiments, distance ranging measurements are passed to the wireless communication-enabled micro-controller (1) through the interface bus (18).

In some embodiments, the integrated gas sensor (10) measures ambient concentrations of total volatile organic compounds and hydrogen ($H_2$) within the cage. In some embodiments, gas concentration data is passed to the wireless communication-enabled micro-controller (1) through the interface bus (18) of the wireless activity and environmental monitoring device.

In some embodiments, the accelerometer/magnetometer (11) measures the orientation of the wireless activity and environmental monitoring device within the cage. In some embodiments, the accelerometer/magnetometer (11) measures changes in orientation and magnitude of accelerations associated with user handling of the cage. The measured orientation and accelerations are passed to the wireless communication-enabled micro-controller (1) through the interface bus (18) of the wireless activity and environmental monitoring device.

In some embodiments, the ambient light photo-transistor (6) measures the relative intensity of ambient visible light within the cage. In some embodiments, the ambient light intensity measurement data is passed to the wireless communication-enabled micro-controller (1) through the interface bus (18) or through an integrated analog-to-digital (ADC) channel on the wireless communication-enabled micro-controller (1).

In some embodiments, information is presented to the user by visual output on a display screen (5). In some embodiments, the display screen (5) is an organic light emitting diode (OLED) display. In some embodiments, the wireless communication-enabled micro-controller (1) controls the display screen (5) through the interface bus (18).

In some embodiments, users of the wireless activity and environmental monitoring device and system input information through user input interface (4), which may include, without limitation, push buttons, capacitative sensors, touch screens, etc. In some embodiments, user input information is passed to the wireless communication-enabled micro-controller (1) through the interface bus (18) or through digital input channels on the wireless communication-enabled micro-controller (1).

In some embodiments, the wireless activity and environmental monitoring device is powered by a battery (14). In some embodiments, the battery (14) is charged from the USB serial interface (2) by a battery charge controller (13). In some embodiments, the battery (14) is charged from an inductive charging coil (19) inductively coupled to an external, powered coil. In some embodiments, the battery voltage is measured by a battery fuel gauge (12), which communicates with the wireless communication-enabled micro-controller (1) through the interface bus (18).

In some embodiments, the electrical components of the wireless activity and environmental monitoring device are integrated onto a single printed circuit board (PCB). In some embodiments, the PCB is placed inside a protective housing (15) which includes an infrared transparent lens (16) and a magnetic mounting (17) for attractive attachment to the cage.

To make the wireless activity and environmental monitoring device and system for small, caged mammals of the present disclosure, a person may assemble the electrical components onto a single PCB using standard soldering techniques. After soldering the electrical components onto the PCB, the person may then connect the battery to the assembled circuit. The person may also place the infrared lens into an aligned recess in the protective housing (14). Then the person may place the assembled circuit inside the protective housing (14) and thereafter close the protective housing (14).

In some embodiments, the distance ranging sensor (8), the T/B/H sensor (9), the gas sensor (10), the battery fuel gauge (11), the protective housing (14), the infrared transparent lens (15), and the magnetic mounting (16) are individually or collectively optional components of the wireless activity and environmental monitoring device.

By way of example, FIG. 1 conceptually illustrates a top perspective view of a wireless activity and environmental monitoring device. As shown in this figure, the wireless activity and environmental monitoring device includes a front housing 10, a plurality of housing button slots 12, a housing screen slot 14, an OLED display screen 30, a plurality of button covers 34, and a rear housing 40.

Now turning to an example with a different view, FIG. 2 conceptually illustrates a bottom perspective view of the wireless activity and environmental monitoring device. As shown in this figure, the wireless activity and environmental monitoring device includes the front housing 10, the plurality of housing button slots 12, the housing screen slot 14, the OLED display screen 30, the plurality of button covers 34, and the rear housing 40. In addition, the bottom perspective view of the wireless activity and environmental monitoring device in this figure demonstrates a location of a USB port, as shown by a USB cover 58 at the bottom edge of the wireless activity and environmental monitoring device.

While the wireless activity and environmental monitoring device is visually illustrated from an outer view in FIGS. 1 and 2, several additional components of the wireless activity and environmental monitoring device are present internally. These internal components are shown by way of example to FIG. 3, which conceptually illustrates a front perspective exploded view of the wireless activity and environmental monitoring device. As shown in this figure, the wireless activity and environmental monitoring device includes the front housing 10, the plurality of housing button slots 12, the housing screen slot 14, the OLED display screen 30, the plurality of button covers 34, the rear housing 40, and the USB cover 58. There are several additional components included within the wireless activity and environmental monitoring device shown in this figure, namely, a plurality of inserts 22, a battery 24, a battery connection post 26, a display screen overlay 28, a display screen spacer 32, a plurality of buttons 36, a pair of magnets 38, a housing USB notch 42, a housing camera slot 44, a housing distance sensor slot 46, a pair of housing magnet slots 52, a plurality of housing screw slots 54, a plurality of screws 56, a circuit board 60, and a programming port 94.

In another view, FIG. 4 conceptually illustrates a rear perspective view of the wireless activity and environmental monitoring device. As shown in this figure, the rear perspective view of the wireless activity and environmental monitoring device reveals the front housing 10, the rear housing 40, the housing camera slot 44, the housing distance sensor slot 46, a housing gas sensor slot 48, a housing T/B/H sensor slot 50, the plurality of screws 56, and the USB cover 58.

Figure 5:
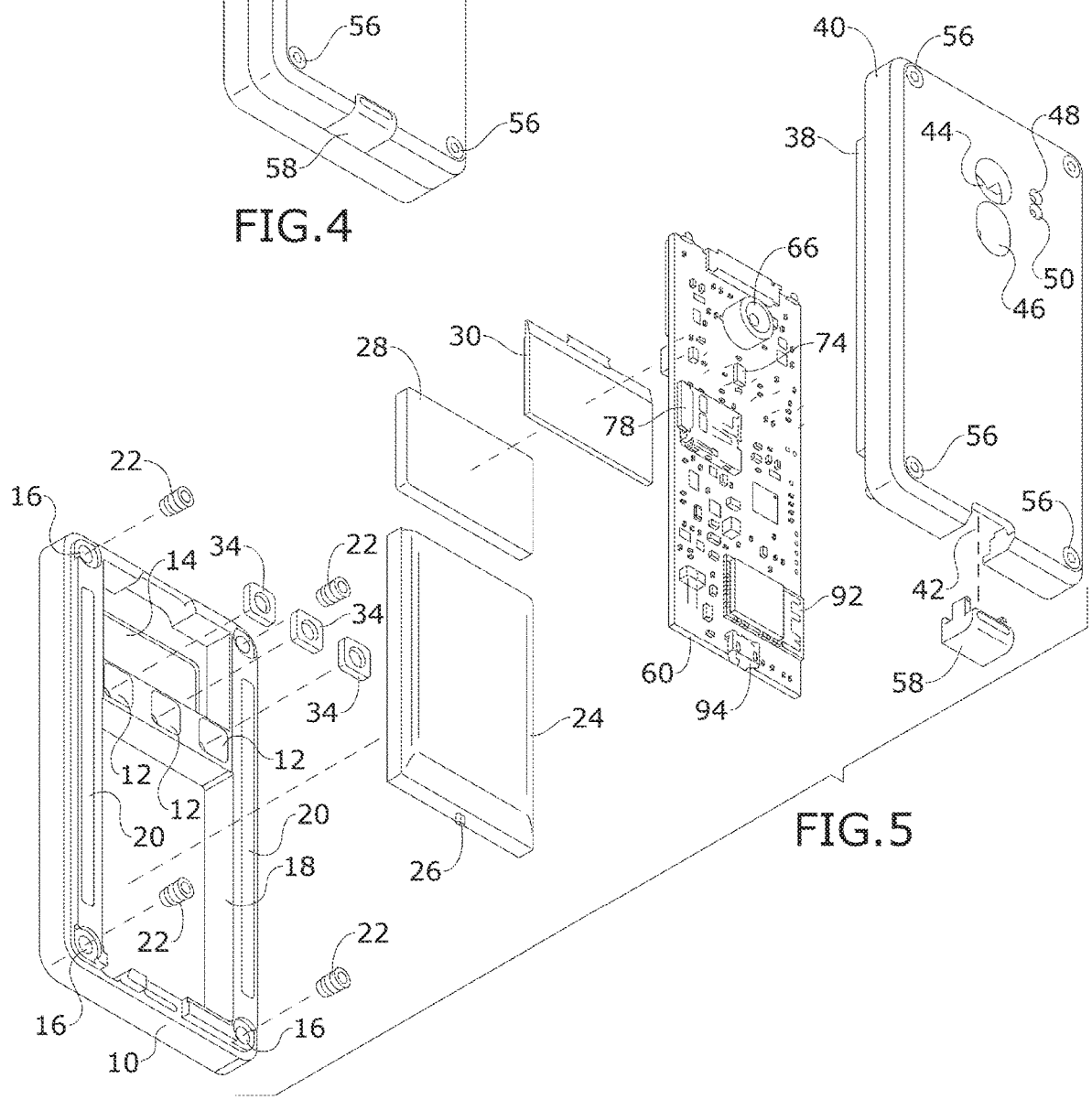
FIG. 5 conceptually illustrates a rear perspective partially exploded view of a wireless activity and environmental monitoring device in some embodiments.

Conceptually similar to the exploded view of the wireless activity and environmental monitoring device described above by reference to FIG. 3, FIG. 5 illustrates a rear perspective partially exploded view of the wireless activity and environmental monitoring device. As shown in this figure, the wireless activity and environmental monitoring device includes the rear housing 40, the circuit board 60, the OLED display screen 30, the display screen overlay 28, the battery 24, the front housing 10, and several other components which are described in connection with one of the rear housing 40, the circuit board 60, the battery 24, and the front housing 10. Specifically, in connection with the rear housing 40, the wireless activity and environmental monitoring device shown in this figure further includes magnets 38, the housing USB notch 42, the housing camera slot 44, the housing distance sensor slot 46, the housing gas sensor slot 48, the housing T/B/H sensor slot 50, the plurality of screws 56, and the USB cover 58. In connection with the circuit board 60, the wireless activity and environmental monitoring device shown in this figure further includes the thermal camera 66, the distance sensor 74, a memory card 78, a wireless communication module 92, and the programming port 94. Now, in connection with the battery 24, the wireless activity and environmental monitoring device shown in this figure further includes the battery connection post 26. In connection with the front housing 10, the wireless activity and environmental monitoring device shown in this figure further includes the plurality of housing button slots 12, the housing display screen slot 14, the plurality of housing insert slots 16, the housing battery slot 18, the pair of housing magnet slots 20, the plurality of inserts 22, and the plurality of button covers 34.

Now turning to another figure, FIG. 6 is a section view of the wireless activity and environmental monitoring device taken along line 6-6 in FIG. 1. As shown in this figure, the wireless activity and environmental monitoring device includes the front housing 10, the housing battery slot 18, the battery 24, the battery connection post 26, the display screen overlay 28, the OLED display screen 30, the display screen spacer 32, button covers 34, buttons 36, the rear housing 40, the housing camera slot 44, the housing distance sensor slot 46, the USB cover 58, the circuit board 60, the thermal camera 66, the distance sensor 74, the microprocessor 82, the wireless communication module 92, and the programming port 94.

By way of another example, FIG. 7 is a section view of the wireless activity and environmental monitoring device taken along line 7-7 in FIG. 6. As shown in this figure, the wireless activity and environmental monitoring device includes the magnets 38, the rear housing 40, the screws 56, the USB cover 58, the circuit board 60, a first LED indicator 62, a second LED indicator 64, the thermal camera 66, a real-time clock 68, a gas sensor 70, a T/B/H sensor 72, the distance sensor 74, a light sensor 76, the memory card 78, an accelerometer/magnetometer 80, the microprocessor 82, the battery gauge 84, a voltage regulator 86, an on/off controller 88, a battery charger 90, the wireless communication module 92, and the programming port 94.

By way of example, FIG. 8 conceptually illustrates a perspective view of a small mammal cage 96 on which to utilize a wireless activity and environmental monitoring device. As shown in this example, the front housing 10 and the OLED display screen 30 appear facing up with the rear housing 40 disposed atop the small mammal cage 96. This configuration allows the wireless activity and environmental monitoring device to be in conjunction with the small mammal cage 96 as a wireless activity and environmental monitoring device and system for small, caged mammals.

Specifically, to use the wireless activity and environmental monitoring device and system of the present disclosure, a user may start by powering on the wireless activity and environmental monitoring device, selecting one or more recording program options through the user input interface (4), and mounting the wireless activity and environmental monitoring device to an interior surface of an animals' cage (such as the standard small animal home cage shown in the figures). In this way, the range of the animals' activity is contained within the field of view of the thermographic sensor. The wireless activity and environmental monitoring device will then monitor animal health and activity unsupervised, saving measurement data to local device data storage (3) and/or wireless transmitting the measurement data to a nearby computing device (e.g., via Bluetooth wireless communication) or to a network computing resource (e.g., via connected WiFi communication) such as a network attached storage (NAS) device, a network file server, a cloud data storage repository, a server computing device, etc. To end operation of the wireless activity and environmental monitoring device and system, the user simply retrieves the wireless activity and environmental monitoring device from the animal home cage and stops the recording program via the user input interface (4).

Figure 9:
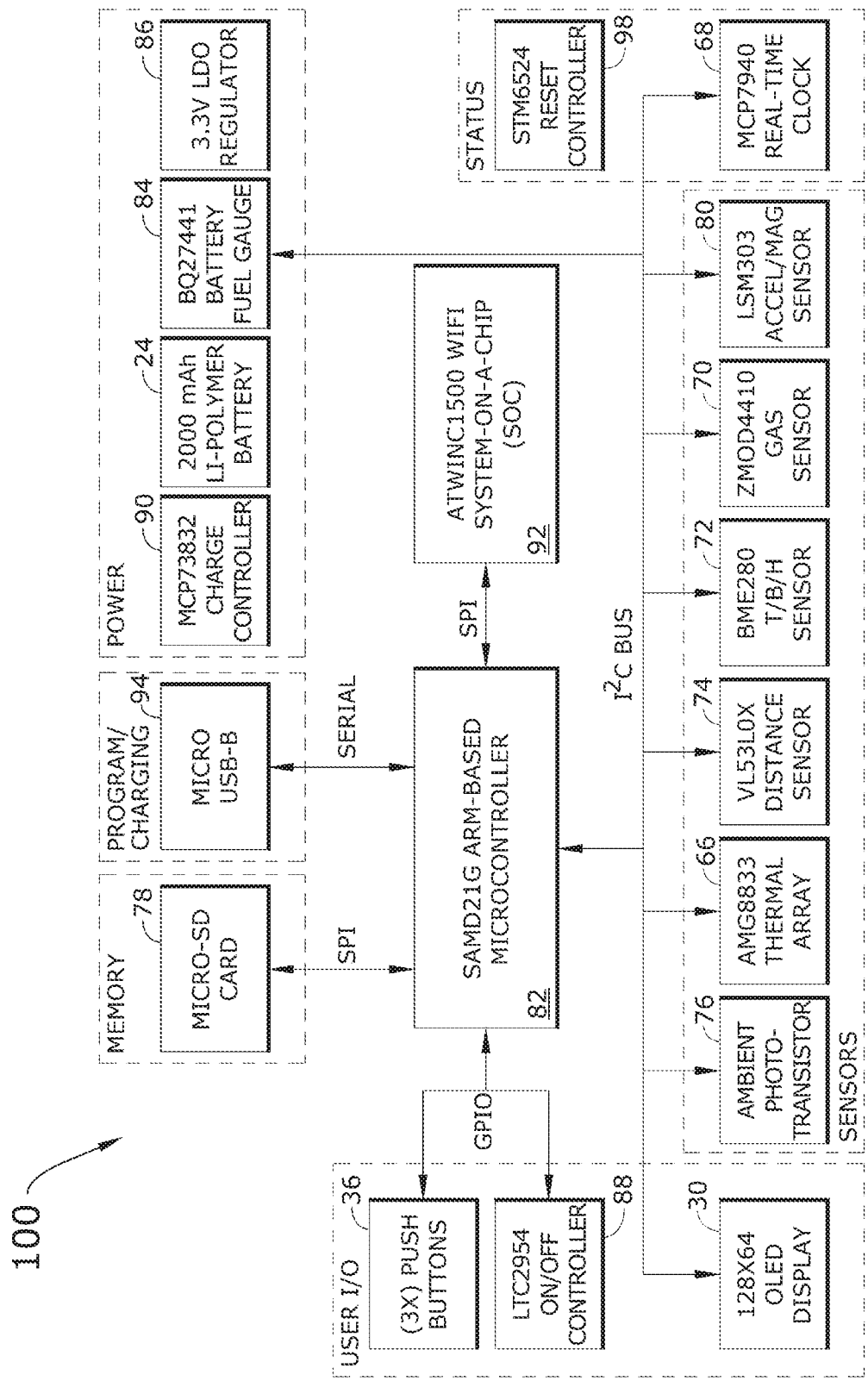
FIG. 9 conceptually illustrates a schematic view of a system architecture of a wireless activity and environmental monitoring device and system for small, caged mammals in some embodiments.

By way of example, FIG. 9 conceptually illustrates a schematic view of a system architecture 100 of a preferred embodiment of the wireless activity and environmental monitoring device for use in connection with the small animal cage 96 as a system for small, caged mammals. As shown in this figure, the system architecture 100 of the preferred embodiment of the wireless activity and environmental monitoring device includes a micro-SD memory card 78, a micro USB-B programming port 94 that is also capable of electronically charging the wireless activity and environmental monitoring device, a MCP73832 battery charge controller 90, a 2000 mAh Li-polymer battery 24, a BQ27441 battery fuel gauge 84, a 3.3V LDO voltage regulator 86, a SAMD21G ARM-based micro-controller 82, a ATWINC1500 WiFi system-on-chip (SoC) wireless communication module 92, a plurality of push buttons 36, a LTC2954 on/off controller 88, an OLED display screen 30 with 128×64 resolution, a MCP7940 real-time clock 68, a STM6524 reset controller 98, and a plurality of sensors comprising an ambient photo-transistor light sensor 76, an AMG8833 thermal array 66 (as a thermal camera), a VL53L0X distance ranging sensor 74, a BME280 T/B/H sensor 72, a ZMOD4410 gas sensor 70, and a LSM303 accelerometer/magnetometer 80.

In some embodiments, an SPI is present between the micro-SD memory card 78 and the SAMD21G ARM-based micro-controller 82 that allows for real-time writing to and reading from memory during processing. In some embodiments, a serial connection is available between the micro USB-B programming port 94 and the SAMD21G ARM-based micro-controller 82 that allows a programmer to access embedded software loaded in memory and/or running on the SAMD21G ARM-based micro-controller 82. In some embodiments, an SPI connection is present between the SAMD21G ARM-based micro-controller 82 and the ATWINC1500 WiFi SoC wireless communication module 92. In some embodiments, general purpose input/output (GPIO) connections are present between the SAMD21G ARM-based micro-controller 82 and each of the plurality of push buttons 36, and the on/off controller 88. In some embodiments, the I$^2$C interface bus connects the SAMD21G ARM-based micro-controller 82 to the OLED display screen 30, the plurality of sensors, and the real-time clock 68.

Although the details described above, in reference to FIG. 9, demonstrate a system architecture 100 of a preferred embodiment of the wireless activity and environmental monitoring device and system for small, caged mammals, a person of ordinary skill in the relevant art may recognize that other system architectures and designs are possible and may be implemented and deployed. Furthermore, many of the above-described features and applications of the wireless activity and environmental monitoring device and system for small, caged mammals are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 10:
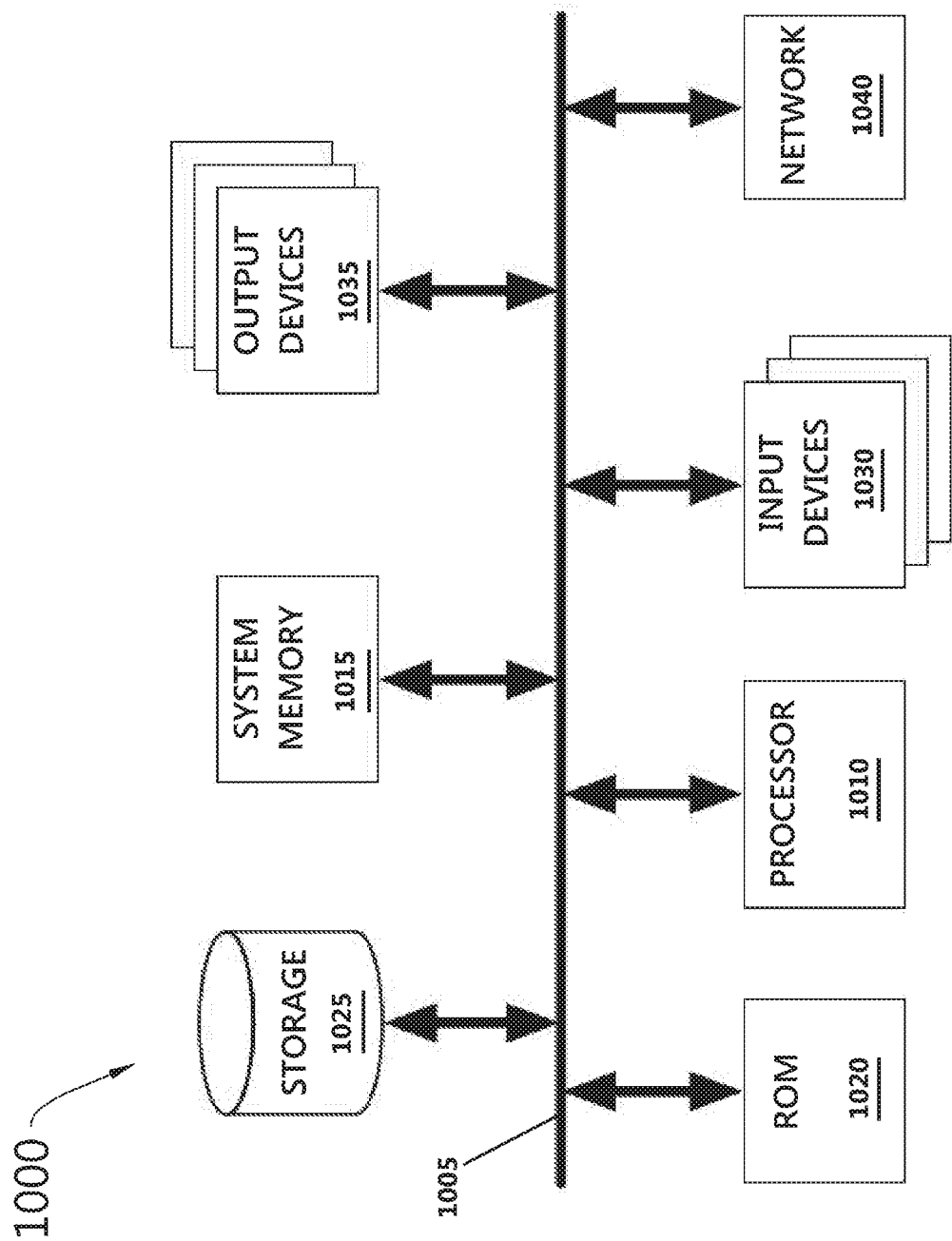
FIG. 10 conceptually illustrates an electronic system with which some embodiments of the invention are implemented.

FIG. 10 conceptually illustrates an electronic system 1000 with which some embodiments of the invention are implemented. The electronic system 1000 may be a computer, phone, PDA, or any other sort of electronic device. Such an electronic system includes various types of computer readable media and interfaces for various other types of computer readable media. Electronic system 1000 includes a bus 1005, processing unit(s) 1010, a system memory 1015, a read-only 1020, a permanent storage device 1025, input devices 1030, output devices 1035, and a network 1040.

The bus 1005 collectively represents all system, peripheral, and chipset buses that communicatively connect the numerous internal devices of the electronic system 1000. For instance, the bus 1005 communicatively connects the processing unit(s) 1010 with the read-only 1020, the system memory 1015, and the permanent storage device 1025.

From these various memory units, the processing unit(s) 1010 retrieves instructions to execute and data to process in order to execute the processes of the invention. The processing unit(s) may be a single processor or a multi-core processor in different embodiments.

The read-only-memory (ROM) 1020 stores static data and instructions that are needed by the processing unit(s) 1010 and other modules of the electronic system. The permanent storage device 1025, on the other hand, is a read-and-write memory device. This device is a non-volatile memory unit that stores instructions and data even when the electronic system 1000 is off. Some embodiments of the invention use a mass-storage device (such as a magnetic or optical disk and its corresponding disk drive) as the permanent storage device 1025.

Other embodiments use a removable storage device (such as a floppy disk or a flash drive) as the permanent storage device 1025. Like the permanent storage device 1025, the system memory 1015 is a read-and-write memory device. However, unlike storage device 1025, the system memory 1015 is a volatile read-and-write memory, such as a random access memory. The system memory 1015 stores some of the instructions and data that the processor needs at runtime. In some embodiments, the invention's processes are stored in the system memory 1015, the permanent storage device 1025, and/or the read-only 1020. For example, the various memory units include instructions for processing appearance alterations of displayable characters in accordance with some embodiments. From these various memory units, the processing unit(s) 1010 retrieves instructions to execute and data to process in order to execute the processes of some embodiments.

The bus 1005 also connects to the input and output devices 1030 and 1035. The input devices enable the user to communicate information and select commands to the electronic system. The input devices 1030 include alphanumeric keyboards and pointing devices (also called "cursor control devices"). The output devices 1035 display images generated by the electronic system 1000. The output devices 1035 include printers and display devices, such as cathode ray tubes (CRT) or liquid crystal displays (LCD). Some embodiments include devices such as a touchscreen that functions as both input and output devices.

Finally, as shown in FIG. 10, bus 1005 also couples electronic system 1000 to a network 1040 through a network adapter (not shown). In this manner, the computer can be a part of a network of computers (such as a local area network ("LAN"), a wide area network ("WAN"), or an intranet), or a network of networks (such as the Internet). Any or all components of electronic system 1000 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

I claim:

1. A wireless activity and environmental monitoring device for unobtrusively monitoring ambient environment conditions and health of a small mammal in an animal home cage, said wireless activity and environmental monitoring device comprising:
   a protective housing comprising a front housing, a plurality of housing insert slots at corners of the front housing, a plurality of inserts that fit within the plurality of housing insert slots, a plurality of housing button slots cut through the front housing, a housing screen slot cut through the front housing, a plurality of front housing magnets embedded within a plurality of front magnet slots within the front housing, a rear housing, a plurality of rear housing magnets embedded within a plurality of rear magnet slots within the rear housing, a plurality of housing screw slots at corners of the rear housing, a plurality of screws that are configured to secure the rear housing to the front housing when screwed through the housing screw slots and into the inserts that fit within the housing insert slots, a housing camera slot cut through the rear housing, a housing distance sensor slot cut through the rear housing, a housing gas sensor slot cut through the rear housing, and a housing temperature-barometric-pressure-humidity (T/B/H) sensor slot cut through the rear housing;
   a printed circuit board (PCB) that is encapsulated within the protective housing;
   an interface bus that is encapsulated within the protective housing and is configured to provide primary data communication between a plurality of sensors and components of the wireless activity and environmental monitoring device;
   a thermographic sensor in the plurality of sensors that is encapsulated within the protective housing and is configured to capture multipixel radiant heat images from infrared emission within the animal home cage;
   a distance ranging sensor in the plurality of sensors that is encapsulated within the protective housing and exposed through the housing distance sensor slot of the rear housing, wherein the distance ranging sensor is configured to measure distance from the wireless activity and environmental monitoring device to a nearest perpendicular opposing surface;
   a temperature-barometric-pressure-humidity (T/B/H) sensor in the plurality of sensors that is encapsulated within the protective housing and exposed through the housing T/B/H sensor slot of the rear housing, wherein the T/B/H sensor is configured to measure ambient temperature, atmospheric pressure, and humidity within the animal home cage;
   a gas sensor in the plurality of sensors that is encapsulated within the protective housing and exposed through the housing gas sensor slot of the rear housing, wherein the gas sensor is configured measure ambient concentrations of total volatile organic compounds and hydrogen ($H_2$) within the animal home cage;
   an ambient light photo-transistor in the plurality of sensors that is encapsulated within the protective housing and is configured to measure relative intensity of ambient visible light within the animal home cage;
   a nonvolatile data memory storage that is attached to the PCB and encapsulated within the protective housing, said data memory storage comprising at least one of flash memory, ferroelectric random access memory (FRAM), static random access memory (SRAM), and magnetoresistive random-access memory (MRAM);
   a display screen that is attached to the PCB in alignment with the housing screen slot cut through the front housing, wherein the display screen is configured to visually output information and sensor data captured by the plurality of sensors for presentation that is visible to a user through the housing screen slot;
   a USB serial interface and connector that is attached to the PCB and is configured to provide battery power to the wireless activity and environmental monitoring device;
   a user input interface comprising a plurality of push buttons attached to the PCB and covered by a plurality of button covers that are exposed to the user through the plurality of housing button slots when the rear housing is secured to the front housing, wherein the plurality of push buttons are activated by touch pressure applied by the user to the plurality of button covers, wherein activation of any push button in the plurality of push buttons triggers an interaction comprising one of navigation through a plurality of program selections that are visually output onto the display screen and selection of a particular program in the plurality of program selections;

a battery that is encapsulated within the protective housing and is configured to provide power to electronically operate the wireless activity and environmental monitoring device;

a battery charge controller that is encapsulated within the protective housing and is configured to charge the battery;

a wireless communication-enabled micro-controller comprising an embedded WiFi data communication module, wherein the wireless communication-enabled micro-controller is attached to the PCB and encapsulated within the protective housing, wherein the embedded WiFi data communication module is configured to connect directly to local wireless networks for uploading data and status information to one or more network resources;

a battery fuel gauge that is encapsulated within the protective housing and is configured to measure battery voltage of the battery and communicate with the wireless communication-enabled micro-controller through the interface bus;

a thermal camera comprising an infrared transparent lens that is aligned toward the rear housing and oriented to face out of the housing camera slot to expose the animal home cage to the lens within a set field of view to capture multipixel radiant heat images from infrared emission within the animal home cage, wherein the thermal camera is connected to the thermographic sensor; and a magnetic mounting that aligns the protective housing of the wireless activity and environmental monitoring device in an orientation with the front housing facing away from the animal home cage and the rear housing facing into the animal home cage when the plurality of front housing magnets are aligned with the plurality of rear housing magnets to magnetically attach to the animal home cage.

2. The wireless activity and environmental monitoring device of claim 1 further comprising an inductive charging coil coupled to an external, powered coil.

3. The wireless activity and environmental monitoring device of claim 2, wherein the battery charge controller charges the battery by way of at least one of the USB serial interface and the inductive charging coil coupled to the external, powered coil.

4. The wireless activity and environmental monitoring device of claim 1, wherein the thermographic sensor comprises at least one of a forward-looking infrared (FLIR) camera and an array of thermopiles.

5. The wireless activity and environmental monitoring device of claim 1, wherein the distance ranging sensor is configured to measure distance by at least one of sonic-based technology and light-based technology.

6. The wireless activity and environmental monitoring device of claim 1, wherein the plurality of push buttons comprises an up push button to navigate up through the plurality of program selections, a down push button to navigate down through the plurality of program selections, and a select push button to select the particular program in the plurality of program selections.

7. The wireless activity and environmental monitoring device of claim 6, wherein the wireless communication-enabled micro-controller collects particular sensor data obtained by particular sensors in the plurality of sensors over the interface bus, wherein the particular sensor data collected comprises (a) thermal image data captured by the thermographic sensor in connection with the thermal camera, (b) distance to the nearest perpendicular opposing surface measured by the distance ranging sensor, (c) ambient temperature, atmospheric pressure, and humidity data measured within the animal home cage by the T/B/H sensor, (d) ambient concentrations of total volatile organic compounds and hydrogen ($H_2$) within the animal home cage measured by the gas sensor, and (e) relative intensity of ambient visible light within the animal home cage measured by the ambient light photo-transistor.

8. The wireless activity and environmental monitoring device of claim 7, wherein the wireless communication-enabled micro-controller further analyzes and processes the particular sensor data including identifying pixels in the thermal image data with measured radiant temperature values significantly above background radiant temperature to measure body surface temperature of the small mammal and to approximate a position of the small mammal within the animal home cage.

9. The wireless activity and environmental monitoring device of claim 8, wherein the wireless communication-enabled micro-controller further saves the particular sensor data onto the data memory storage via the interface bus, visually outputs the particular sensor data on the display screen for viewing by the user through the housing screen slot of the front housing, and wirelessly transmits the particular sensor data to a network resource by the embedded WiFi data communication module.

10. The wireless activity and environmental monitoring device of claim 9, wherein the wireless communication-enabled micro-controller further monitors each of the push buttons in the plurality of push buttons for touch pressure applied by the user to the button covers corresponding to the push buttons, wherein the user input interface triggers a push button activation event that is detected by the wireless communication-enabled micro-controller and which corresponds to one of a navigation action and a user selection action of a particular program in the plurality of program selections.

* * * * *